US00PP32309P2

(12) United States Plant Patent
Hermans

(10) Patent No.: US PP32,309 P2
(45) Date of Patent: Oct. 13, 2020

(54) *BUXUS* PLANT NAMED 'HER2010B02'

(50) Latin Name: *Buxus*
Varietal Denomination: HER2010B02

(71) Applicant: Herplant BVBA, Beerse (BE)

(72) Inventor: Didier Hermans, Beerse (BE)

(73) Assignee: HERPLANT BVBA, Beerse (NL)

( * ) Notice: Subject to any disclaimer, the term of this patent is extended or adjusted under 35 U.S.C. 154(b) by 0 days.

(21) Appl. No.: 16/602,567

(22) Filed: Oct. 31, 2019

(51) Int. Cl.
*A01H 5/00* (2018.01)

(52) U.S. Cl.
USPC ..... Plt./226

(58) Field of Classification Search
USPC ..... Plt./226
CPC ..... A01H 5/00
See application file for complete search history.

(56) References Cited

PUBLICATIONS

PLUTO Plant Variety Database Apr. 23, 2020. p. 1.*

* cited by examiner

*Primary Examiner* — Annette H Para
(74) *Attorney, Agent, or Firm* — Penny J. Aguirre

(57) ABSTRACT

A new cultivar of *Buxus* plant named 'HER2010B02' that is characterized by its medium sized bushy, upright plant habit, its leaves that are small, glossy and medium green color, medium sized hedges and for shearing into topiary forms, its suitability for use medium sized hedges and for shearing into topiary forms, and its resistance to *Calonectria pseudonaviculata* (box blight).

2 Drawing Sheets

Botanical classification: *Buxus* hybrid.
Variety denomination: 'HER2010B02'.

CROSS REFERENCE TO A RELATED APPLICATIONS

This application is co-pending with a U.S. Plant Patent Application filed for plants derived from the same breeding program that are entitled *Buxus* Plant Named 'HER2009B01' (U.S. Plant patent application Ser. No. 16/602,565). *Buxus* Plant Named 'HER2009B03' (U.S. Plant patent application Ser. No. 16/602,568), and *Buxus* Plant Named 'HER2010B04' (U.S. Plant patent application Ser. No. 16/602,566). This application is related to a European plant breeders' rights application filed on Apr. 23, 2018, application No. 2018/1124. There have been no offers for sale anywhere in the world prior to the effective filing date of this Application and no accessibility to one of ordinary skill in the art could have been derived from the printed plant breeder's rights documents.

BACKGROUND OF THE INVENTION

The present invention relates to a new and distinct cultivar of *Buxus* of hybrid origin and will be referred to hereafter by its cultivar name, 'HER2010B02'. 'HER2010B02' is a new cultivar of boxwood grown for use as an ornamental landscape plant and particularly useful as a medium sized hedge and for shearing into topiary forms.

The new cultivar was developed from an ongoing breeding program conducted under the direction of the Inventor at his nursery in Lilsedijk, Beerse, Belgium. 'HER2010B02' arose from crosses made between un named and unpatented proprietary seedlings for *Buxus* from the Inventor's breeding program in 2009 and 2010. The seeds from various crosses were pooled and the exact parentage is unknown. The resulting seedlings underwent bio assay tests followed by field examinations to initially make selections that showed good resistance against *Calonectria pseudonaviculata* (box blight). The Inventor selected the new cultivar as a single unique plant from amongst the seedlings of the above crosses in 2015.

Asexual propagation of the new cultivar was first accomplished under the direction of the Inventor by stem cuttings in 2015 in Lilsedijk, Beerse, Belgium. Asexual propagation of the new cultivar by stem cuttings has determined that the characteristics are stable and are reproduced true to type in successive generations.

SUMMARY OF THE INVENTION

The following traits have been repeatedly observed and represent the characteristics of the new cultivar. These attributes in combination distinguish 'HER2010B02' as a unique cultivar of *Buxus*.

1. 'HER2010B02' exhibits a medium sized bushy, upright plant habit.
2. 'HER2010B02' exhibits leaves that are small, glossy and medium green color.
3. 'HER2010B02' exhibits suitability for use medium sized hedges and for shearing into topiary towers.
4. 'HER2010B02' exhibits resistance to *Calonectria pseudonaviculata* (box blight).

'HER2009B03' can be most closely compared to typical plants of *Buxus sempervirens* and *Buxus* cultivars derived from the same breeding; 'HER2009B03', 'HER2009B01', and 'HER2010B04'. Typical plants of *Buxus sempervirens* are similar to 'HER2010B02' in plant size and plant habit but differ from 'HER2010B02' in having leaves that are larger, lighter green, and in being very susceptible to box blight. 'HER2009B03', 'HER2009B01', and 'HER2010B04' are all similar to 'HER2010B02' in having resistance to box blight. 'HER2009B03' differs from 'HER2010B02' in having a taller plant height and faster growth rate. 'HER2009B01' differs from 'HER2010B02' in having a low growing plant habit and a slower growth rate. 'HER2010B04' differs from 'HER2010B02' in having a spreading growth habit and stems that are slightly twisted and leaves that are moderately to strongly undulate.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosure includes but may not be limited to a catalogue listing in 2019 for availability in 2020 by Herplant.

BRIEF DESCRIPTION OF THE DRAWINGS

The accompanying colored photographs illustrate the overall appearance and distinct characteristics of the new *Buxus*. The photographs were taken of a plant 8.5 years in age as grown outdoors in a 5-gallon container at a nursery in Beerse, Belgium.

The photograph in FIG. 1 provides a side view of the plant habit of 'HER2010B02'.

Figure 1:
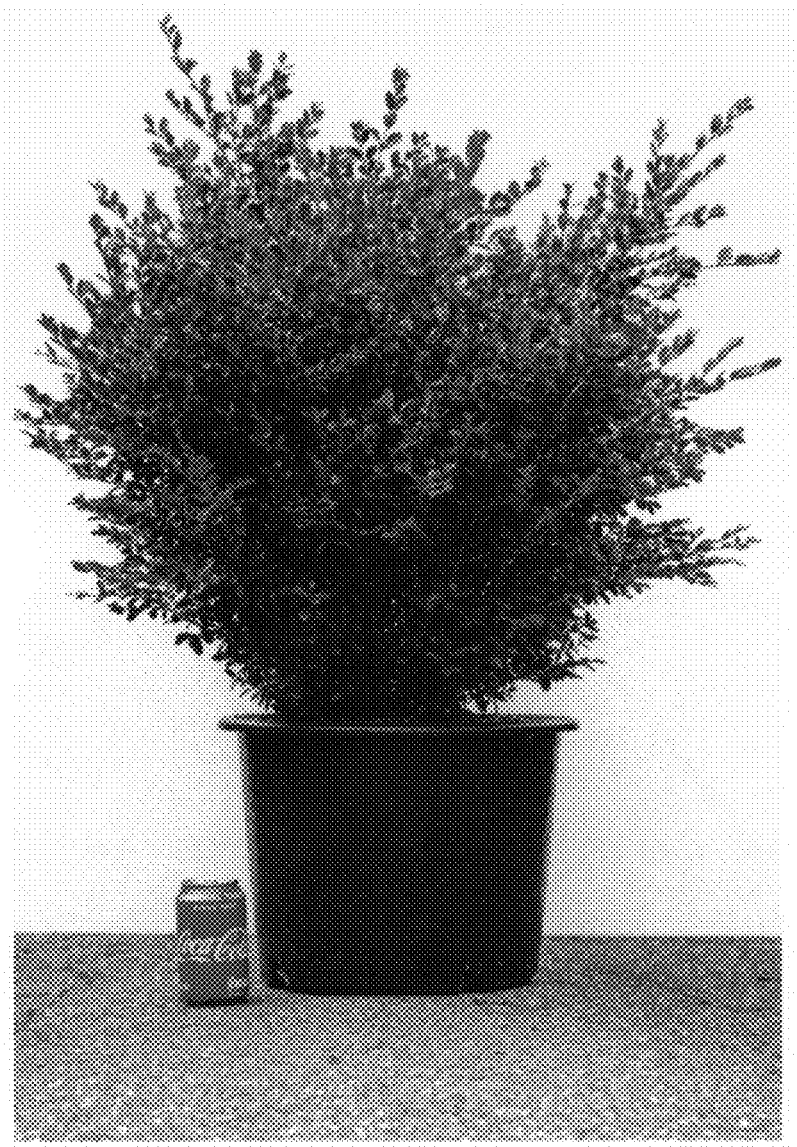
Figure 2:
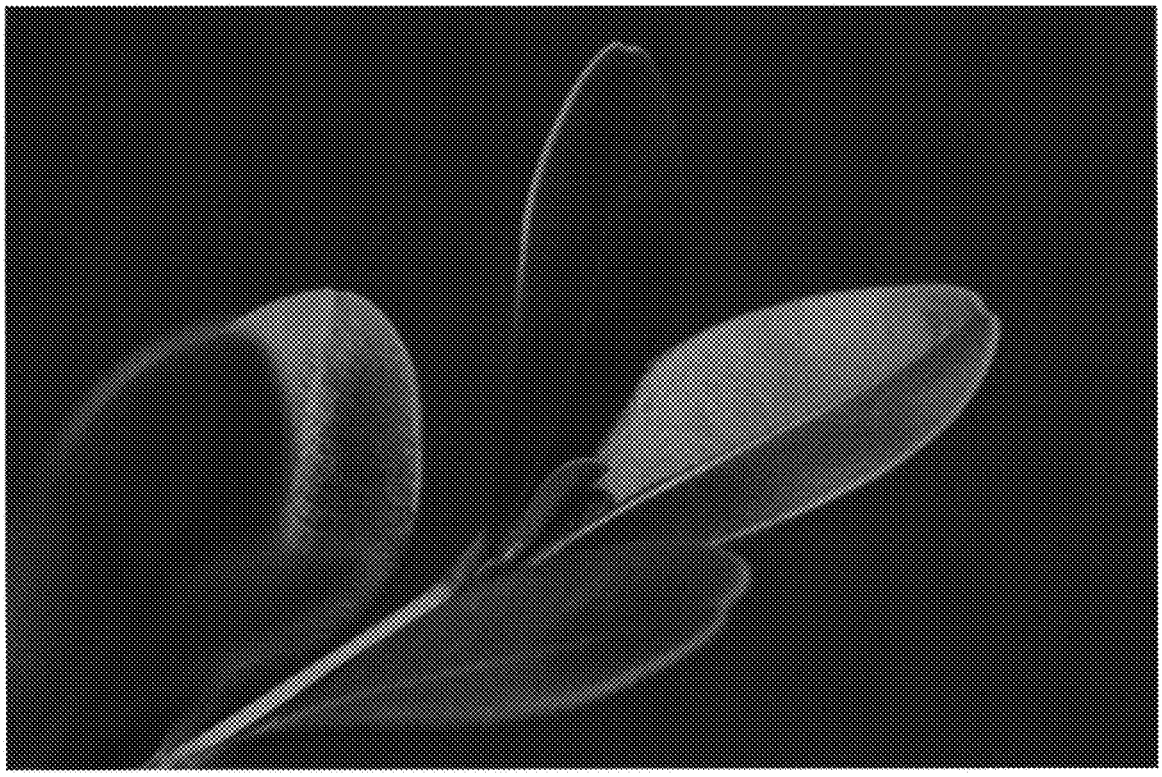

The photograph in FIG. 2 provides a close-up view of the foliage of 'HER2010B02'.

The colors in the photographs are as close as possible with the photographic and printing technology utilized and the color values cited in the detailed botanical description accurately describe the colors of the new *Buxus*.

DETAILED BOTANICAL DESCRIPTION

The following is a description of 3-year-old plants as grown outdoors in 17-cm containers in Beerse, Belgium. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type*.—Evergreen shrub.

*Plant habit*.—Medium sized, bushy, spreading.

*Plant shape*.—Broad obovate.

*Height and spread*.—Reaches an average of 18.8 cm in height, 19.9 cm in diameter as grown in a 17-cm container, reached 100 cm in height and 50 cm in width as an 8.5-year-old plant as grown outdoors in a 5-gallon container.

*Hardiness*.—At least in U.S.D.A. Zones 6 to 10.

*Diseases resistance*.—Resistance to *Calonectria pseudonaviculata* (Box Blight).

*Root description*.—Fibrous, 161A in color.

*Propagation*.—Stem cuttings.

*Root development*.—Cutting taken in mid-July initiate roots in 6 to 8 weeks with a young rooted plant produced in 8 to 10 weeks.

*Growth rate*.—Moderate to high.

Branch description:

*Branch shape*.—Quadrangular, four narrow wings average of 0.3 mm in width.

*Branch color*.—Young; 144A, mature; 143A to 143B, bark and older; 161D.

*Branch aspect*.—Average of 37.5° to vertical.

*Branch size*.—9.4 cm in length, 1.5 mm in diameter.

*Branch strength*.—Strong.

*Branch surface*.—Very slightly glossy.

*Branch number*.—An average of 3 main stems, average of 18 lateral branches.

*Branching habit*.—Freely branching.

*Internode length*.—Average of 1.5 cm.

Foliage description:

*Leaf shape*.—Elliptic to broadly elliptic and slightly obovate.

*Leaf division*.—Simple.

*Leaf arrangement*.—Opposite.

*Leaf base*.—Narrow acute.

*Leaf aspect*.—Slightly carinate.

*Leaf apex*.—Un-deeply emarginate to obtuse.

*Leaf fragrance*.—Light fresh fragrance.

*Leaf venation*.—Pinnate, midrib; upper surface 143A, lower surface same as leaf color and densely covered with small glands NN155B in color.

*Leaf margins*.—Entire, occasionally slightly undulate.

*Leaf arrangement*.—Opposite.

*Leaf attachment*.—Petiolate.

*Leaf surface*.—Both surfaces smooth, glabrous, glossy and non-rugose.

*Leaf texture*.—Both surfaces smooth and glabrous.

*Leaf size*.—An average of 1.8 cm in length and 1 cm in width.

*Leaf quantity*.—Average of 14 (7 pairs).

*Leaf color*.—Young upper surface; 143A to 144A, young lower surface 144B, mature upper surface; between NN137A and 147A, mature lower surface 143B to 144B.

*Petioles*.—Average of 1 mm in length and width, both surfaces glabrous and slightly glossy, strong, upper surface color 144A, lower surface color 143A.

Inflorescence description: No flowers have been observed.

It is claimed:

1. A new and distinct cultivar of *Buxus* plant named 'HER2010B02' as herein illustrated and described.

* * * * *